United States Patent
Voth

(10) Patent No.: US 10,714,218 B2
(45) Date of Patent: Jul. 14, 2020

(54) METHODS AND SYSTEMS FOR DISPLAYING ELECTROPHYSIOLOGICAL LESIONS

(71) Applicant: St. Jude Medical, Cardiology Division, Inc., St. Paul, MN (US)

(72) Inventor: Eric J. Voth, Maplewood, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 16/355,240

(22) Filed: Mar. 15, 2019

(65) Prior Publication Data

US 2019/0214148 A1 Jul. 11, 2019

Related U.S. Application Data

(63) Continuation of application No. 15/279,572, filed on Sep. 29, 2016, now Pat. No. 10,276,267.

(Continued)

(51) Int. Cl.
| | |
|---|---|
| *G16H 50/50* | (2018.01) |
| *G06T 19/20* | (2011.01) |
| *A61B 34/10* | (2016.01) |
| *A61B 5/01* | (2006.01) |
| *A61B 5/00* | (2006.01) |
| *A61B 18/00* | (2006.01) |
| *A61B 90/00* | (2016.01) |

(52) U.S. Cl.
CPC ............ *G16H 50/50* (2018.01); *A61B 5/015* (2013.01); *A61B 5/6852* (2013.01); *A61B 34/10* (2016.02); *G06T 19/20* (2013.01); *A61B 2018/00351* (2013.01); *A61B 2018/00357* (2013.01); *A61B 2018/00779* (2013.01); *A61B 2018/00791* (2013.01); *A61B 2018/00886* (2013.01); *A61B 2034/101* (2016.02); *A61B 2034/104* (2016.02); *A61B 2034/105* (2016.02); *A61B 2090/065* (2016.02)

(58) Field of Classification Search
CPC ........ G16H 50/50; A61B 34/10; A61B 5/015; A61B 5/6852
See application file for complete search history.

(56) References Cited

U.S. PATENT DOCUMENTS

| | | |
|---|---|---|
| 6,233,476 B1 | 5/2001 | Strommer et al. |
| 6,498,944 B1 | 12/2002 | Ben-Haim et al. |

(Continued)

OTHER PUBLICATIONS

Teschner, Michael, et al. "Texture Mapping: A New Tool for Molecular Graphics", Journal of molecular graphics 12.2 (1994): 98-105.

*Primary Examiner* — Sarah Lhymn
(74) *Attorney, Agent, or Firm* — Armstrong Teasdale LLP

(57) ABSTRACT

The present disclosure provides systems and methods for rendering lesions on a geometric surface model of a geometric structure. The system includes a computer-based model construction system configured to create a three-dimensional (3D) texture map including a plurality of voxels each having a tissue necrosis value, increment the tissue necrosis values as a function of at least one parameter to generate a total tissue necrosis value for each voxel, render at least one lesion on the geometric surface model based on the total tissue necrosis values, and display the geometric surface model and the at least one rendered lesion.

16 Claims, 8 Drawing Sheets

Related U.S. Application Data

(60) Provisional application No. 62/237,850, filed on Oct. 6, 2015.

(56) References Cited

U.S. PATENT DOCUMENTS

| | | |
|---|---|---|
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |
| 8,638,328 B2 | 1/2014 | Lin |
| 2007/0018993 A1 | 1/2007 | Levene et al. |
| 2009/0221999 A1* | 9/2009 | Shahidi .............. A61B 18/1815 606/33 |
| 2010/0298826 A1 | 11/2010 | Leo et al. |
| 2012/0029504 A1 | 2/2012 | Afonso et al. |
| 2012/0123400 A1* | 5/2012 | Francischelli ......... A61B 18/12 606/20 |
| 2014/0012155 A1 | 1/2014 | Flaherty et al. |
| 2015/0087927 A1 | 3/2015 | Manzke et al. |
| 2015/0112321 A1 | 4/2015 | Cadouri |
| 2017/0243364 A1* | 8/2017 | Carmi ....................... G06T 7/45 |

\* cited by examiner

METHODS AND SYSTEMS FOR DISPLAYING ELECTROPHYSIOLOGICAL LESIONS

CROSS-REFERENCE TO RELATED APPLICATIONS

This application is a continuation of U.S. patent application Ser. No. 15/279,572 filed on Sep. 29, 2016, entitled "METHODS AND SYSTEMS FOR DISPLAYING ELECTROPHYSIOLOGICAL LESIONS", which claims the benefit of priority to U.S. Provisional Patent Application No. 62/237,850 filed on Oct. 6, 2015, entitled "METHODS AND SYSTEMS FOR DISPLAYING ELECTROPHYSIOLOGICAL LESIONS," the entire contents and disclosures of which are hereby incorporated herein by reference in their entirety.

FIELD OF THE DISCLOSURE

This disclosure relates to systems and methods for generating an electrophysiological map of a geometric structure. More particularly, this disclosure relates to computer-implemented systems and methods for rendering lesions on a model of a geometric structure, such as, for example, an intra-cardiac structure.

BACKGROUND

It is known that various computer-based systems and computer-implemented methodologies can be used to generate multi-dimensional surface models of geometric structures, such as, for example, anatomic structures. More specifically, a variety of systems and methods have been used to generate multi-dimensional surface models of the heart and/or particular portions thereof.

At least some known systems facilitate displaying lesions (e.g., generated from ablation therapy) on generated surface models. In some known systems, lesions are rendered as either brown spheres or brown surface patches, with a user-selectable radius. The locations of the rendered lesions are determined solely based on user placement. That is, the lesions are not rendered based on potentially relevant parameter values such as power level, delivery duration, tissue contact force, lesion-size index (LSI), or force-time integral (FTI). Accordingly, it would be desirable to display lesions more accurately using multi-dimensional modeling systems.

BRIEF SUMMARY OF THE DISCLOSURE

In one embodiment, the present disclosure is directed to a system for rendering lesions on a geometric surface model of a geometric structure. The system includes a computer-based model construction system configured to create a three-dimensional (3D) texture map including a plurality of voxels each having a tissue necrosis value, increment the tissue necrosis values as a function of at least one parameter to generate a total tissue necrosis value for each voxel, render at least one lesion on the geometric surface model based on the total tissue necrosis values, and display the geometric surface model and the at least one rendered lesion.

In another embodiment, the present disclosure is directed to a computer-implemented method of rendering lesions on a geometric surface model of a geometric structure. The method includes creating a three-dimensional (3D) texture map including a plurality of voxels each having a tissue necrosis value, incrementing the tissue necrosis values as a function of at least one parameter to generate a total tissue necrosis value for each voxel, rendering at least one lesion on the geometric surface model based on the total tissue necrosis values, and displaying the geometric surface model and the at least one rendered lesion.

In another embodiment, the present disclosure is directed to a processing apparatus for rendering lesions on a geometric surface model of a geometric structure. The processing apparatus is configured to create a three-dimensional (3D) texture map including a plurality of voxels each having a tissue necrosis value, increment the tissue necrosis values as a function of at least one parameter to generate a total tissue necrosis value for each voxel, render at least one lesion on the geometric surface model based on the total tissue necrosis values, and display the geometric surface model and the at least one rendered lesion.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for rendering lesions on a geometric surface model of a geometric structure (e.g., of a cardiac structure). A computer-based model construction system is configured to create a three-dimensional (3D) texture map including a plurality of voxels each having a tissue necrosis value. The tissue necrosis values are incremented according to at least one parameter to generate a total tissue necrosis value for each voxel. At least one lesion is rendered on the geometric surface model based on the total tissue necrosis values, and the geometric surface model and the at least one rendered lesion are display for a user.

Figure 1:
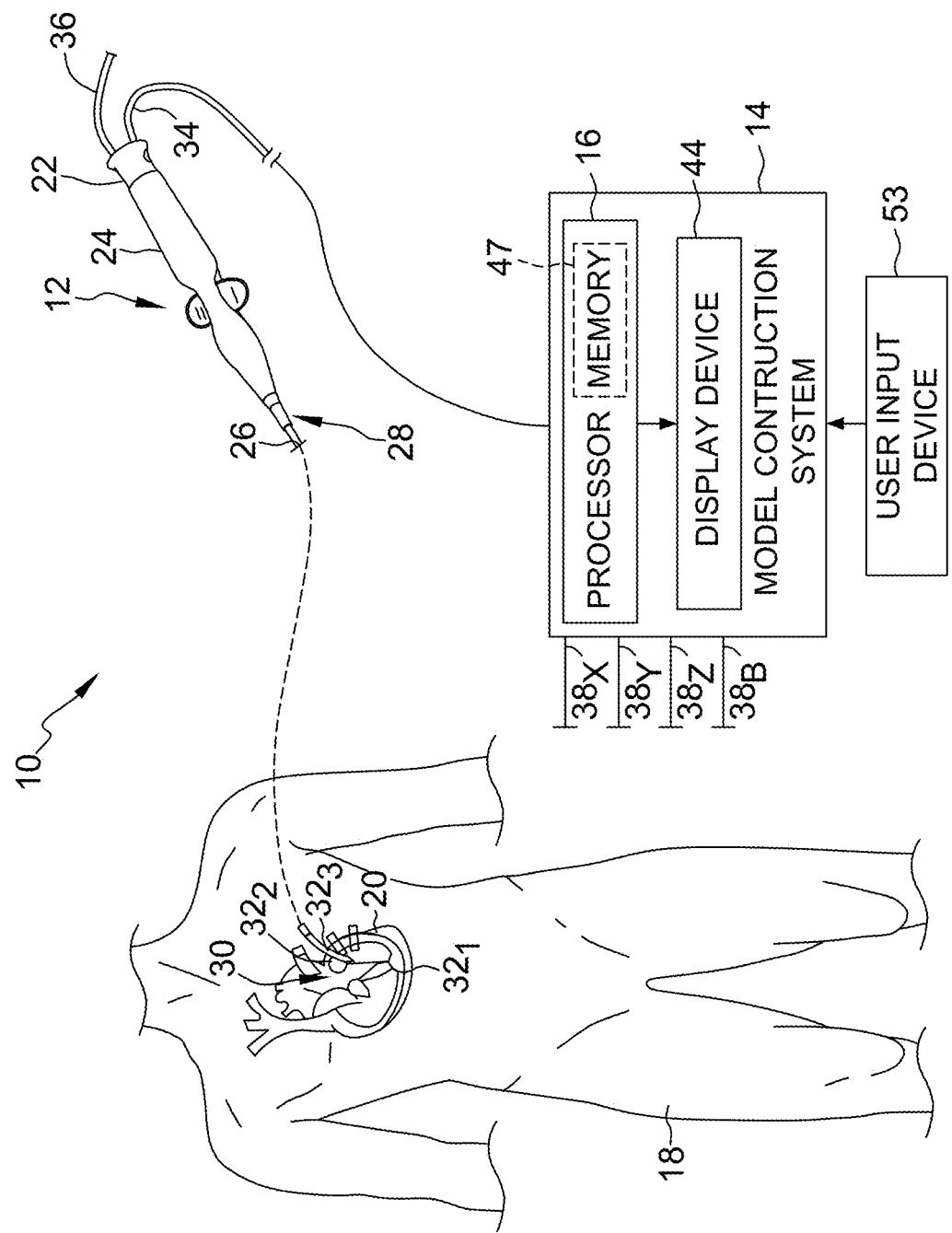
FIG. 1 is a diagrammatic view of a system for generating a multi-dimensional surface model of a geometric structure according to one embodiment.

Referring now to the drawings wherein like reference numerals are used to identify identical components in the various views, FIG. 1 illustrates one exemplary embodiment of a system 10 for generating a multi-dimensional surface model of one or more geometric structures. As will be described below, in this embodiment, the model generated by system 10 is a three-dimensional model. It will be appreciated, however, that while the generation of a three-dimensional model is described below, the present disclosure is not meant to be so limited. Rather, in other embodiments, system 10 may be configured to generate multi-dimensional models other than in three dimensions, and such embodiments remain within the spirit and scope of the present disclosure.

It should be further noted that while the following description focuses primarily on the use of system 10 in the generation of models of anatomic structures, and cardiac structures in particular, the present disclosure is not meant to be so limited. Rather, system 10, and the methods and techniques used thereby, may be applied to the generation of three-dimensional models of any number of geometric structures, including anatomic structures other than cardiac structures. However, for purposes of illustration and ease of description, the description below will be focused on the use of system 10 in the generation of three-dimensional models of cardiac structures.

With continued reference to FIG. 1, in this embodiment, the system 10 includes, among other components, a medical device and a model construction system 14. In this embodiment, medical device is a catheter 12, and model construction system 14 includes, in part, a processing apparatus 16. Processing apparatus 16 may take the form of an electronic control unit, for example, that is configured to construct a three-dimensional model of structures within the heart using data collected by catheter 12.

As illustrated in FIG. 1, catheter 12 is configured to be inserted into a patient's body 18, and more particularly, into the patient's heart 20. Catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient), and one or more sensors 32 (e.g., 32$_1$, 32$_2$, 32$_3$) mounted in or on shaft 26 of catheter 12. In this embodiment, sensors 32 are disposed at or near distal end 30 of shaft 26. Catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

Connector 22 provides mechanical, fluid, and electrical connection(s) for cables, such as, for example, cables 34, 36 extending to model construction system 14 and/or other components of system 10 (e.g., a visualization, navigation, and/or mapping system (if separate and distinct from model construction system 14), an ablation generator, irrigation source, etc.). Connector 22 is conventional in the art and is disposed at proximal end 28 of catheter 12, and handle 24 thereof, in particular.

Handle 24, which is disposed at proximal end 28 of shaft 26, provides a location for the clinician to hold catheter 12 and may further provide means for steering or guiding shaft 26 within body 18 of the patient. For example, handle 24 may include means to change the length of a steering wire extending through catheter 12 to distal end 30 of shaft 26 to steer shaft 26. Handle 24 is also conventional in the art and it will be understood that the construction of handle 24 may vary. In other embodiments, catheter 12 may be robotically driven or controlled. Accordingly, rather than a clinician manipulating a handle to steer or guide catheter 12 and shaft 26 thereof, in such an embodiments, a robot is used to manipulate catheter 12.

Shaft 26 is an elongate, tubular, flexible member configured for movement within body 18. Shaft 26 supports, for example and without limitation, sensors and/or electrodes mounted thereon, such as, for example, sensors 32, associated conductors, and possibly additional electronics used for signal processing and conditioning. Shaft 26 may also permit transport, delivery, and/or removal of fluids (including irrigation fluids, cryogenic ablation fluids, and bodily fluids), medicines, and/or surgical tools or instruments. Shaft 26 may be made from conventional materials such as polyurethane, and defines one or more lumens configured to house and/or transport electrical conductors, fluids, or surgical tools. Shaft 26 may be introduced into a blood vessel or other structure within the body 18 through a conventional introducer. Shaft 26 may then be steered or guided through body 18 to a desired location, such as heart 20, using means well known in the art.

Sensors 32 mounted in or on shaft 26 of catheter 12 may be provided for a variety of diagnostic and therapeutic purposes including, for example and without limitation, electrophysiological studies, pacing, cardiac mapping, and ablation. In this embodiment, one or more of sensors 32 are provided to perform a location or position sensing function. More particularly, and as will be described in greater detail below, one or more of sensors 32 are configured to be a positioning sensor(s) that provides information relating to the location (position and orientation) of catheter 12, and distal end 30 of shaft 26 thereof, in particular, at certain points in time. Accordingly, as catheter 12 is moved along a surface of a structure of interest of heart 20 and/or about the interior of the structure, sensor(s) 32 can be used to collect location data points that correspond to the surface of, and/or other locations within, the structure of interest. These location data points can then be used by, for example, model construction system 14, in the construction of a three-dimensional model of the structure of interest, which will be described in greater detail below. For purposes of clarity and illustration, the description below will discuss an embodiment wherein multiple sensors 32 of catheter 12 comprise positioning sensors. It will be appreciated, however, that in other embodiments, which remain within the spirit and scope of the present disclosure, catheter 12 may comprise both one or more positioning sensors as well as other sensors configured to perform other diagnostic and/or therapeutic functions.

As briefly described above, and as will be described in greater detail below, model construction system 14 is configured to construct a three-dimensional model of structures within the heart using, in part, location data collected by catheter 12. More particularly, processing apparatus 16 of model construction system 14 is configured to acquire location data points collected by sensor(s) 32 and to then use those location data points in the construction or generation of a model of the structure(s) to which the location data points correspond. In this embodiment, model construction system 14 acquires the location data points by functioning with sensors 32 to collect location data points. In other embodiments, however, model construction system 14 may simply acquire the location data points from sensors 32 or another component in system 10, such as, for example, a memory or other storage device that is part of model construction system 14 or accessible thereby, without affirmatively taking part in the collection of the location data points. Model construction system 14 is configured to construct a three-dimensional model based on some or all of the collected location data points. For purposes of illustration and clarity, the description below will be limited to an embodiment wherein model construction system 14 is configured to both construct the model and also acquire location data points by functioning with sensor(s) 32 in the collection of the location data points. It will be appreciated, however, that other embodiments wherein model construction system 14 only acquires location data points from sensor(s) 32 or another component of system 10 and then constructs a three-dimensional model based thereon remain within the spirit and scope of the present disclosure.

Accordingly, in this embodiment, in addition to constructing a model of a structure, model construction system 14 is configured to function with sensor(s) 32 to collect location data points that are used in the construction of a three-dimensional model. Model construction system 14 may comprise an electric field-based system, such as, for example, the EnSite™ NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other embodiments, however, model construction system 14 may comprise other types of systems, such as, for example and without limitation: a magnetic-field based system such as the Carto™ system available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster; as well as other impedance-based localization systems, acoustic or ultrasound-based systems, and commonly available fluoroscopic, computed tomography (CT), and magnetic resonance imaging (MRI)-based systems.

As briefly described above, sensor(s) 32 of catheter 12 include positioning sensors. Sensor(s) 32 produce signals indicative of catheter location (position and/or orientation) information. In this embodiment, wherein model construction system 14 is an electric field-based system, sensor(s) 32 may comprise one or more electrodes. Alternatively, in an embodiment where model construction system 14 is a magnetic field-based system, sensor(s) 32 may include one or more magnetic sensors configured to detect one or more characteristics of a low-strength magnetic field. For instance, in one exemplary embodiment, sensor(s) 32 may include magnetic coils disposed on or in shaft 26 of catheter 12.

For purposes of clarity and illustration, model construction system 14 will hereinafter be described as including an electric field-based system, such as, for example, the EnSite™ NavX™ system identified above. It will be appreciated that while the description below is primarily limited to an embodiment wherein sensor(s) 32 include one or more electrodes, in other embodiments, sensor(s) 32 may include one or more magnetic field sensors (e.g., coils). Accordingly, model construction systems that include positioning sensor(s) other than the sensors or electrodes described below remain within the spirit and scope of the present disclosure.

Figure 2:
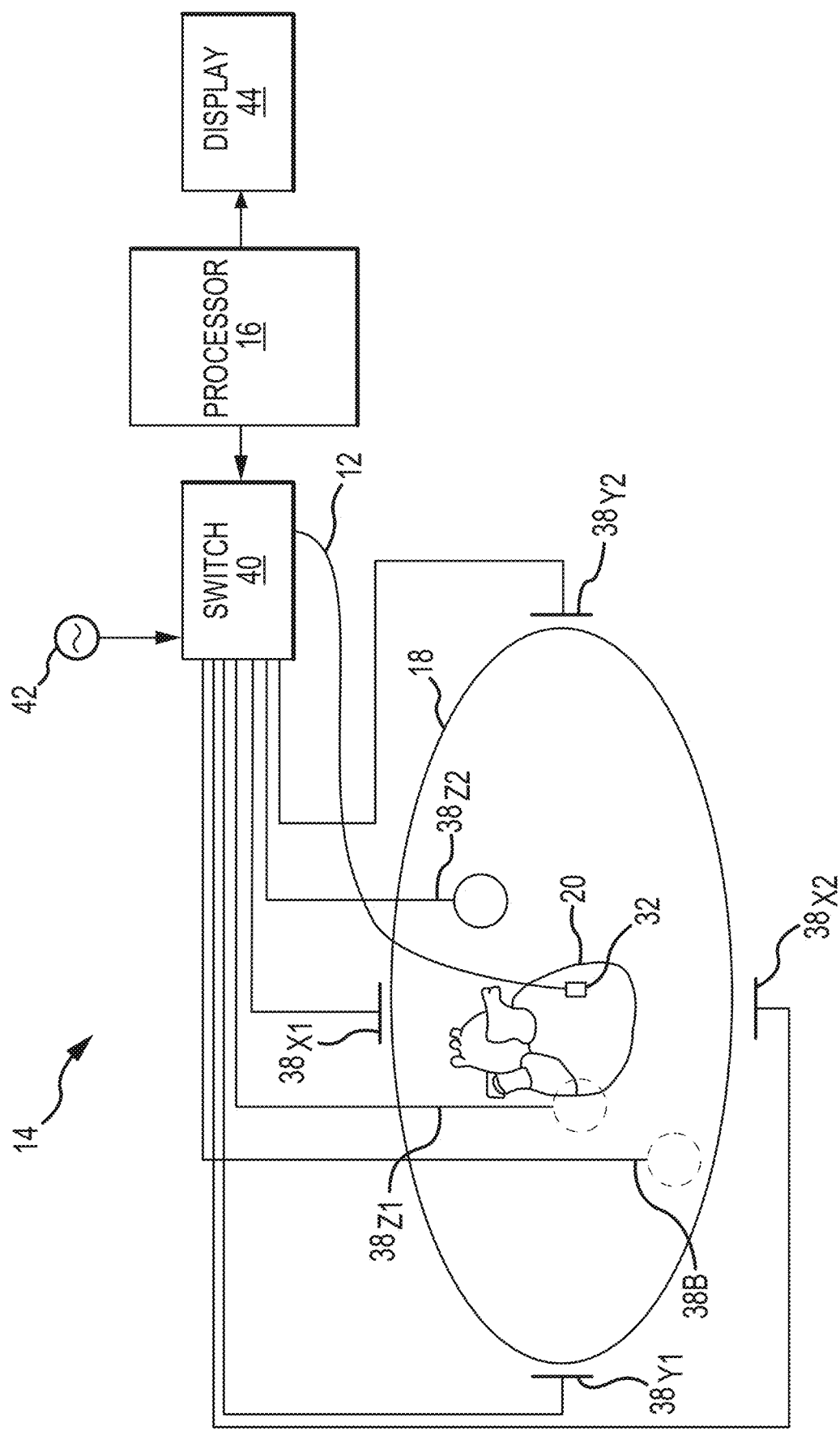
FIG. 2 is a diagrammatic and schematic view of a model construction system of the system illustrated in FIG. 1.

With reference to FIG. 2, in addition to the processing apparatus 16, model construction system 14 may include, among other possible components, a plurality of patch electrodes 38, a multiplex switch 40, a signal generator 42, and a display device 44. In other embodiments, some or all of these components are separate and distinct from model construction system 14 but are electrically connected to, and configured for communication with, model construction system 14.

Processing apparatus 16 may include a programmable microprocessor or microcontroller, or may include an application specific integrated circuit (ASIC). Processing apparatus 16 may include a central processing unit (CPU) and an input/output (I/O) interface through which the processing apparatus 16 may receive a plurality of input signals including, for example, signals generated by patch electrodes 38 and sensor(s) 32, and generate a plurality of output signals including, for example, those used to control and/or provide data to, for example, display device 44 and switch 40. Processing apparatus 16 may be configured to perform various functions, such as those described in greater detail above and below, with appropriate programming instructions or code (i.e., software). Accordingly, processing apparatus 16 is programmed with one or more computer programs encoded on a computer storage medium for performing the functionality described herein.

With the possible exception of patch electrode $38_B$ called a "belly patch," patch electrodes 38 are provided to generate electrical signals used, for example, in determining the position and orientation of catheter 12. In one embodiment, patch electrodes 38 are placed orthogonally on the surface of body 18 and are used to create axes-specific electric fields within body 18. For instance, in one embodiment, patch electrodes $38_{X1}$, $38_{X2}$ may be placed along a first (x) axis. Patch electrodes $38_{Y1}$, $38_{Y2}$ may be placed along a second (y) axis, and patch electrodes $38_{Z1}$, $38_{Z2}$ may be placed along a third (z) axis. Each of patch electrodes 38 may be coupled to multiplex switch 40. In this embodiment, processing apparatus 16 is configured, through appropriate software, to provide control signals to switch 40 to thereby sequentially couple pairs of electrodes 38 to signal generator 42. Excitation of each pair of electrodes 38 generates an electric field within body 18 and within an area of interest such as heart 20. Voltage levels at non-excited electrodes 38, which are referenced to belly patch $38_B$, are filtered and converted and provided to processing apparatus 16 for use as reference values.

In this embodiment, sensor(s) 32 of catheter 12 are electrically coupled to processing apparatus 16 and are configured to serve a position sensing function. More particularly, sensor(s) 32 are placed within electric fields created in body 18 (e.g., within the heart) by exciting patch electrodes 38. For purposes of clarity and illustration only, the description below will be limited to an embodiment wherein a single sensor 32 is placed within electric fields. It will be appreciated, however, that in other embodiments that remain within the spirit and scope of the present disclosure, a plurality of sensors 32 can be placed within the electric fields and then positions and orientations of each sensor can be determined using the techniques described below.

When disposed within the electric fields, sensor 32 experiences voltages that are dependent on the location between patch electrodes 38 and the position of sensor 32 relative to tissue. Voltage measurement comparisons made between sensor 32 and patch electrodes 38 can be used to determine the location of sensor 32 relative to the tissue. Accordingly, as catheter 12 is swept about or along a particular area or surface of interest, processing apparatus 16 receives signals (location information) from sensor 32 reflecting changes in voltage levels on sensor 32 and from the non-energized patch electrodes 38. Using various known algorithms, the processing apparatus 16 may then determine the location (position and orientation) of sensor 32 and record it as a location data point 46 (also referred to herein as "data point 46" and illustrated in FIG. 3) corresponding to a location of sensor 32, and therefore, a point on the surface or in the interior of the structure of interest being modeled, in a memory or storage device, such as memory 47, associated with or accessible by processing apparatus 16. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Further, locations of other portions of catheter 12 may be inferred from measurements at sensors 32, such as by interpolation or extrapolation, to generate further location data points 46. In any event, the collection of location data points 46 ($46_1$, $46_2$, . . . , $46_n$) taken over time results in the formation of a point cloud 48 (best shown in FIG. 3) stored in the memory or storage device.

While the description above has thus far been generally with respect to an orthogonal arrangement of patch electrodes 38, the present disclosure is not meant to be so limited. Rather, in other embodiments, non-orthogonal arrangements may be used to determine the location coordinates of sensor 32. For example, and in general terms, FIGS. 4A-4D depict a plurality of exemplary non-orthogonal dipoles $D_0$, $D_1$, $D_2$, and $D_3$, set in a coordinate system 50. In FIGS. 4A-4D, the X-axis patch electrodes are designated $X_A$ and $X_B$, the Y-axis patch electrodes are designated $Y_A$ and $Y_B$, and the Z-axis patch electrodes are designated $Z_A$ and $Z_B$. For any desired axis, the potentials measured across an intra-cardiac sensor, such as sensor 32, resulting from a predetermined set of drive (source/sink) configurations may be combined algebraically to yield the same effective potential as would be obtained simply by driving a uniform current along the orthogonal axes. Any two of the patch electrodes $38_{X1}$, $38_{X2}$, $38_{Y1}$, $38_{Y2}$, $38_{Z1}$, and $38_{Z2}$ (See FIG. 2) may be selected as a dipole source and drain with respect to a ground reference, e.g., belly patch $38_B$, while the unexcited patch electrodes measure voltage with respect to the ground reference. Sensor 32 placed in heart 20 is also exposed to the field for a current pulse and is measured with respect to ground (e.g., belly patch $38_B$).

In another exemplary embodiment, multiple patch electrodes 38 may be arranged linearly along a common axis. In such an embodiment, excitation of an electrode pair comprising one of patch electrodes 38 and an electrode mounted on catheter 12 generates an electric field. The non-excited patch electrodes 38 may then measure potentials that can be used to determine the position of sensor 32. Accordingly, in such an embodiment, the excitation of multiple electrode pairs comprising different patch electrodes 38 and the catheter-mounted electrode may be used to determine the position of sensor 32.

Data sets from each of patch electrodes 38 and the sensor 32 are all used to determine the location of sensor 32 within heart 20. After the voltage measurements are made, a different pair of patch electrodes 38 is excited by the current source and the voltage measurement process of the remaining patch electrodes 38 and sensor 32 takes place. Once the location of sensor 32 is determined, and as was described above, the location may be recorded as a data point 46 in the same manner described above. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Accordingly, it will be appreciated that any number of techniques may be used to determine locations of sensor 32 and to, therefore, collect data points corresponding thereto, each of which remains within the spirit and scope of the present disclosure.

Figure 3:
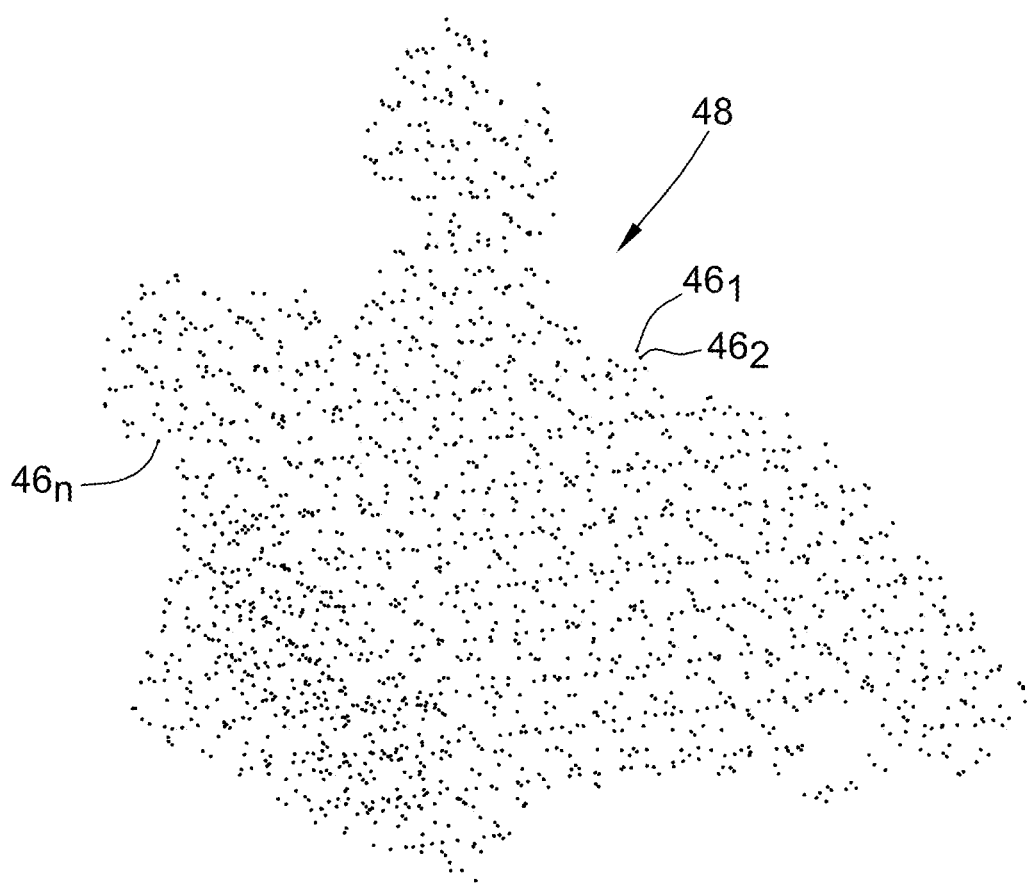
FIG. 3 is a schematic view of a point cloud containing a collection of location data points.
Figure 4A:
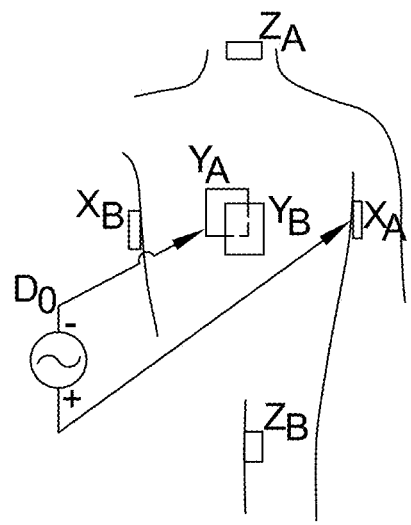
FIGS. 4A-4D are schematic diagrams of exemplary dipole pairs of driven patch electrodes suitable for use in the model construction system illustrated in FIG. 2.
Figure 4B:
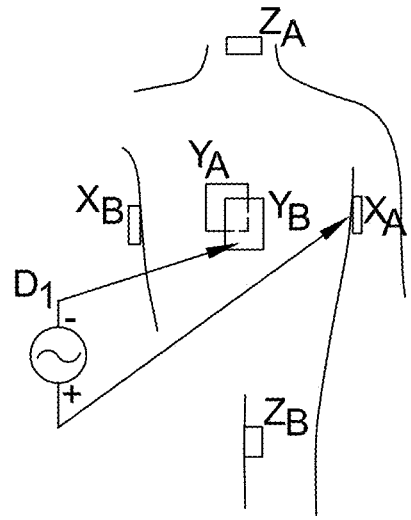
Figure 4C:
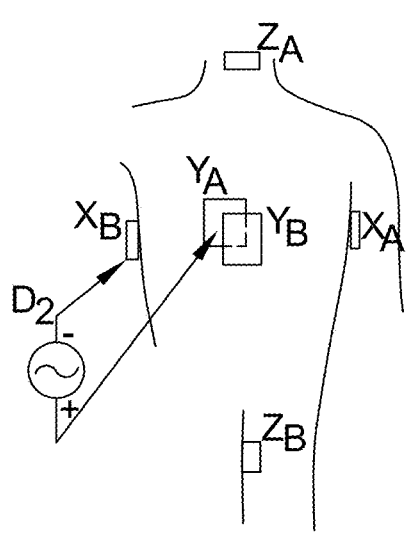
Figure 4D:
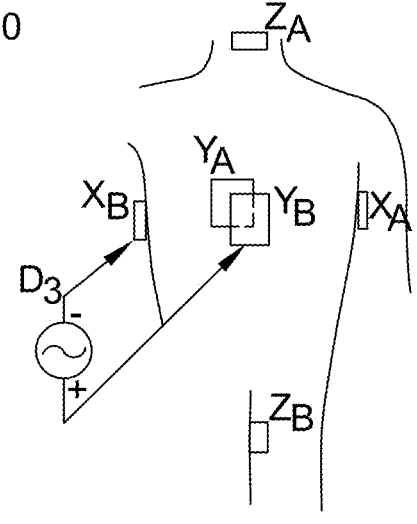

FIG. 3 is illustrative of the point cloud 48 including location data points $46_1$, $46_2$, . . . $46_n$ corresponding to a particular structure of interest being modeled. It will be appreciated that in practice, the point cloud 48 would generally include hundreds to hundreds of thousands of data points 46. For purposes of illustration and ease of description, however, the description below will be limited to a point cloud having a limited number of location data points, such as, for example, point cloud 48 including location data points 46.

As will be appreciated by those skilled in the art, using location data points 46, a geometric surface model of the structure of interest may be generated. Further, as noted above, in at least some known systems, lesions may be rendered on a geometric surface model. However, in at least some known systems, the lesions are not rendered based on parameter values such as power level, delivery duration, tissue contact force, lesion-size index (LSI), and force-time integral (FTI). In contrast, as described below, in the systems and methods described herein, a three-dimensional (3D) texture map is used to include any or all of these parameters. Further, by interfacing with an ablation generator, lesions may be rendered fully automatically by storing a tissue necrosis value for each voxel in the 3D texture map and indexing it into a 1D (or 2D) texture map for display.

Figure 5:
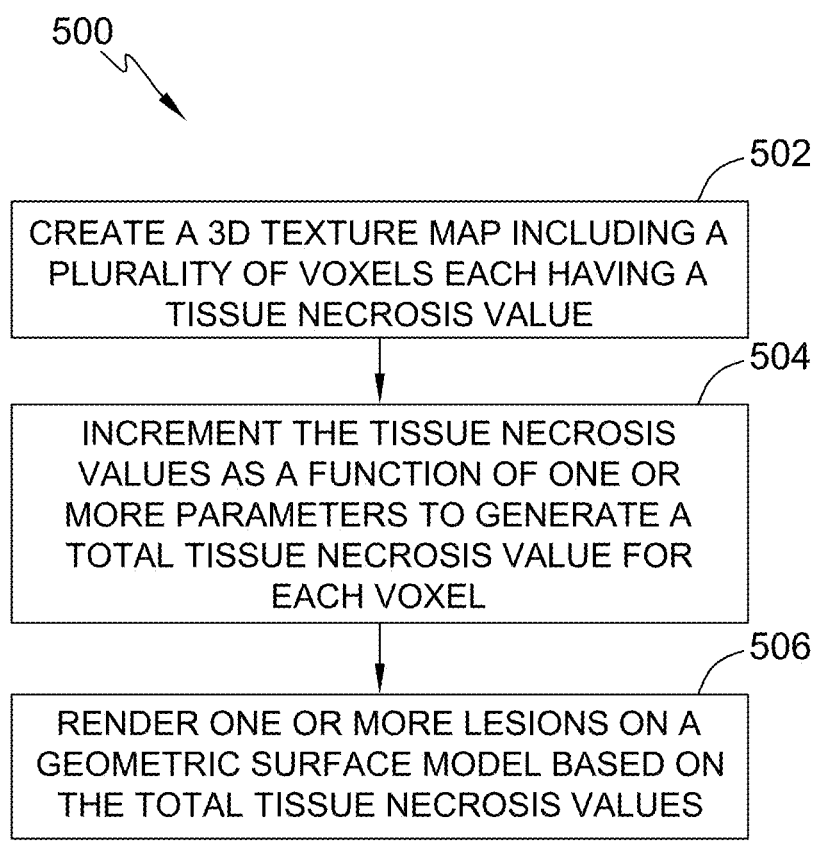
FIG. 5 is a flowchart of a method for rendering lesions on a geometric surface model according to one embodiment.

FIG. 5 is a flowchart of one embodiment of a method 500 for rendering lesions on a geometric surface model. In the example embodiment, in step 502, a scalar 3D texture map is created. As will be understood by one of skill in the art, a texture map is an image (typically 2D, but possibly 1D or 3D) that is "painted" onto a polygon while the polygon is being drawn by graphics hardware. Each vertex of the polygon has coordinates in (x, y, z) space, in addition to one or more coordinates in the texture map, which describe the portion of the texture map that gets painted onto that polygon. For example, using texture maps, the effect of clouds or grass may be represented by drawing just a few polygons for the sky or ground, without having to draw each wisp of cloud or blade of grass as its own colored polygon (which would require significantly more computational resources).

The 3D texture map created in step 502 is large enough to include an entire bounding volume of the geometry model. Further, the 3D texture map is a lattice of voxels that each have an associated tissue necrosis value. In one embodiment, the 3D texture map has a 0.5 millimeter (mm) resolution over its entire volume. Alternatively, the 3D texture map may have any suitable resolution.

In step 504, the tissue necrosis value of each voxel in the 3D map that is within a given distance of an ablation location (e.g., the 3D location of an ablation electrode or the projection of the 3D location of the ablation electrode onto the geometric surface model) is incremented as a function of one or more parameters to generate a total tissue necrosis value. The parameters may include, distance from the ablation location, ablation power level, contact force, tissue temperature, etc. For example, the tissue necrosis values may be incremented as a function of at least one of a power level, a delivery duration, a tissue contact force, a lesion-size index, and a force-time integral associated with an ablation procedure. Further, the values for the parameters may be acquired, for example, using an instrument that applies ablation to generate the lesions. Accordingly, the lesions may be rendered in real-time as the ablation is occurring. The incrementing function may be based on physiological theory, simulation, and/or experimental results. Further, the function may vary over time as well as distance.

In step 506, the one or more lesions are rendered on the geometric surface model based on the total tissue necrosis values. Specifically, in this embodiment, the total tissue necrosis values are indexed into a relatively small 1D (or 2D) texture map. The 1D (or 2D) texture map may range from transparent (optionally with a reddish tinge) to a tannish or light burnt color. Storing the total necrosis value for each voxel allows neighboring lesions to merge into one another when rendered, with a single border zone, which is clinically accurate. Further, the border zone may transition from opaque to transparent, appearing "fuzzy" to emphasize that map data underneath may be of questionable validity. Where the border zone is fully transparent (i.e., further away from the center of the lesion), any underlying electrophysiological data that is displayed (e.g., peak voltage, local activation time, fractionation value, and/or any other clinically useful measurement or computation) will be displayed in its full natural color. In contrast, closer to the center of the lesion, the border zone becomes opaque, and the color of the electrophysiological data will be obscured by the color of the lesion.

Notably, if the 3D texture map has a sufficiently small resolution (e.g., 0.5 mm), the lesions may be displayed accurately, and multiple lesions or parts thereof may be rendered on the same facet of the geometric surface model, independent of the geometry resolution or facet size. The lesions may be rendered directly on the geometric surface model itself, or may be rendered on a separate overlay layer (e.g., an offset surface that is slightly displaced in a normal direction relative to the geometric surface model, and that is transparent in regions where there are no lesions). The overlay layer could be selectively displayed independent from the underlying geometric surface model in some embodiments.

The ablation location used to render a lesion may vary over time, resulting in a "spray-painting" effect for the rendered lesion. Further, in the systems and methods described herein, there is no need to use a "lesion-breaking" algorithm to determine where one lesion ends and another begins. Instead, adjacent lesions are continuous in space, which is more biophysically realistic than the spheres or surface patches rendered using at least some known methods.

In some embodiments, each voxel in the 3D texture map also contains a stored tissue temperature value associated with that voxel location. This tissue temperature value is incremented by a clinically relevant function and may take into account the temperature of neighboring points to mimic heat conduction. In some embodiments, when ablative RF energy is removed, the relevant voxels could "cool down" to full health (e.g., a tissue necrosis value of zero), some predetermined level of necrosis, or complete death, depending on the maximum temperature achieved. Further, if ablative RF energy is restarted, the temperature would begin rising again from its current level. Those of skill in the art will appreciate that parameters other than temperature may also be associated with each voxel (e.g., tissue type, total energy delivered, power level, delivery duration, tissue contact force, LSI, and FTI). For example, tissue type could be used in conjunction with temperature to determine the degree of tissue necrosis. That is, differences in heat absorption/dissipation due to specific characteristics of the tissue (e.g., thicker ventricular cardiac tissue as compared to thinner ventricular cardiac tissue) could be taken into account.

To generate the lesions, at step 506, triangles of the geometric surface model are drawn using each geometric vertex of the triangles as an index into the 3D texture map of tissue necrosis values. The resulting value may be used as an index into the 1D (or 2D) lesion texture map. That is, the geometry vertices are used as the texture coordinates to get the correct color index into the lesion spectrum. To facilitate improving rendering speed, for step 506, in some embodiments, the tissue necrosis and/or temperature value may be incremented in a relatively thin two-dimensional region surrounding the geometry model, instead of in full 3D. In another embodiment, the geometry could first be rendered into an empty 3D texture map to create a bitfield of texture voxels that intersect the surface model, since those are the only texture points that need to be colored. In yet another embodiment, to increase the rendering speed, the actual 3D necrosis texture map may be used as the bitfield. The bitfield may be initialized to −1.0, and the graphics hardware or geometry renderer could draw the surface model into this texture map to set voxels intersecting the surface to an initial weight of 0.0. From then on during the procedure, the tissue necrosis values would only need to be computed for voxels that have a nonnegative weight.

In some embodiments, scar/fibrosis information may be incorporated from an external imaging modality (e.g., late gadolinium enhancement magnetic resonance imaging (LGE MRI)) into this framework. If such an image is voxelized according to the fraction of scar/fibrosis information and properly registered to the geometry model, that information could be loaded directly into a texture map and rendered on the surface, along with the original mapping data and lesions.

Figure 6:
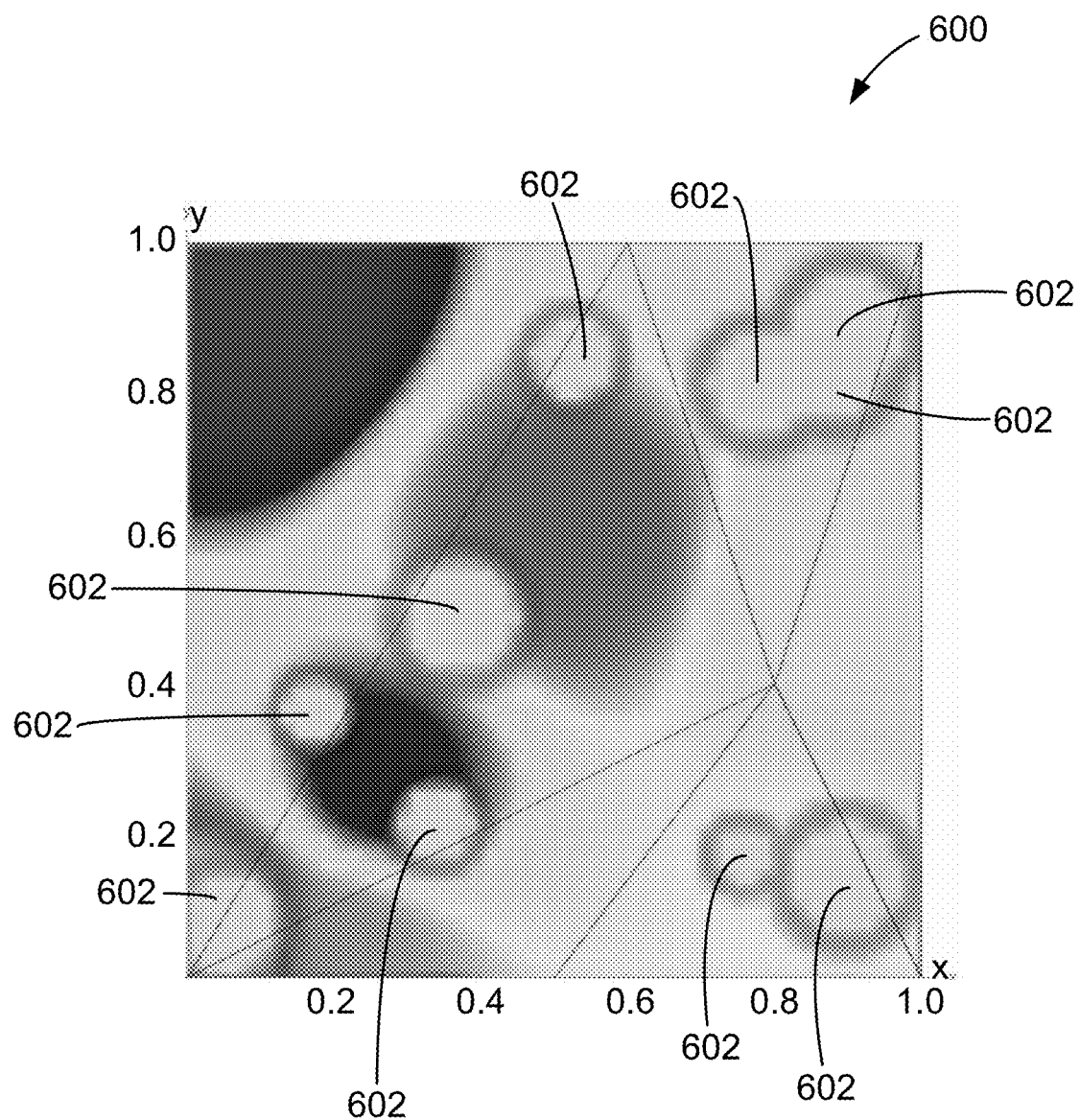
FIG. 6 is an example of a map including lesions that is generated using the method illustrated in FIG. 5.
Figure 7:
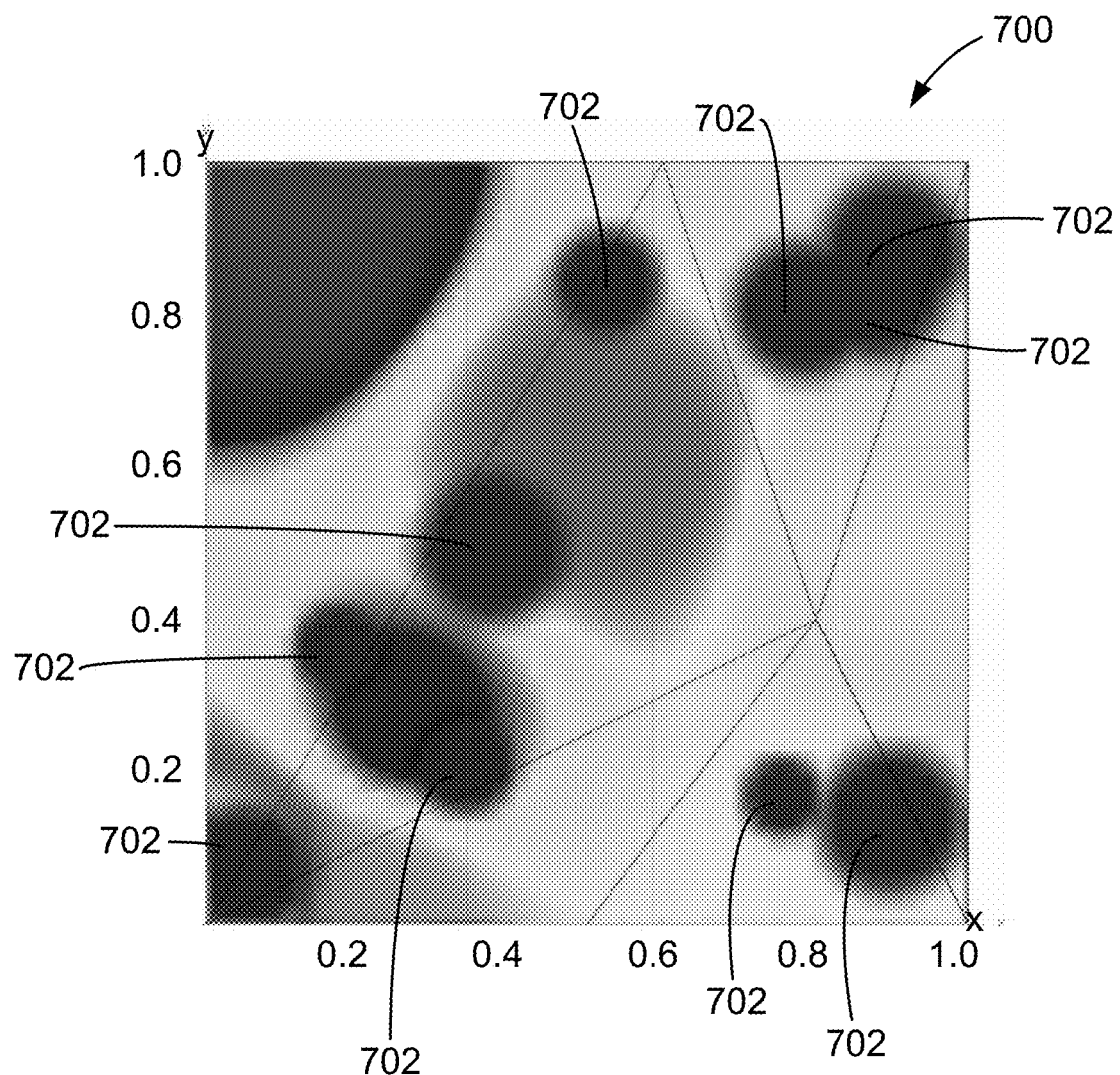
FIG. 7 is an example of a map including lesions that is generated using the method illustrated in FIG. 5.
Figure 8:
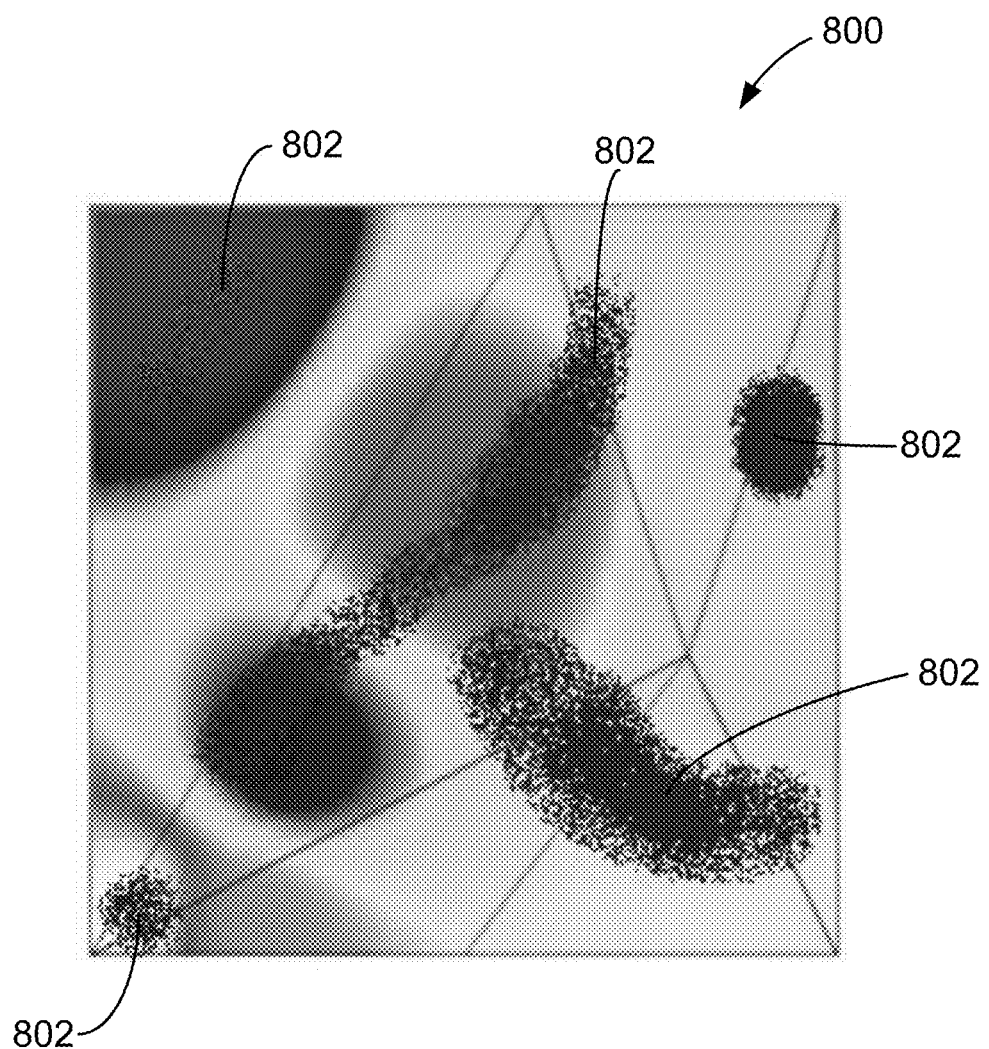
FIG. 8 is an example of a map including lesions that is generated using the method illustrated in FIG. 5.

Notably, the lesions may be rendered using any suitable size, color function, border zone, translucency, and/or sharpness. For example, FIGS. 6 and 7 are example maps 600 and 700 generated using the systems and methods described herein. In map 600, lesions 602 are rendered as substantially white, with a reddish tinged border zone. In map 700, lesions 702 are rendered as substantially brown. As shown in maps 600 and 700, lesions 602 and 702 as rendered overlap in a natural and visually intuitive way. Notably, to generate maps 600 and 700, the triangles are being rendered one vertex at a time, while all colormap interpolation is being handled in texture memory on a graphics card. As explained above, the ablation location may also vary over time, resulting in a "spray-painting" effect for the rendered lesion. FIG. 8 is an example map 800 that includes lesions 802 generated with a varying ablation location. Maps 600, 700, and 800 all facilitate providing users with real-time feedback on energy delivery/lesion coverage during an ablation procedure.

It should be understood that model construction system 14, and particularly processing apparatus 16, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in some embodiments, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for rendering lesions on a geometric surface model of a geometric structure, the system comprising:
    a computer-based model construction system configured to be coupled to a device that includes at least one sensor configured to acquire a set of original location data points to facilitate generating the geometric surface model, the computer-based model construction system further configured to:
        create a three-dimensional (3D) texture map including a plurality of voxels each having a tissue necrosis value;
        determine an ablation location;
        identify, from the plurality of voxels, all voxels that are within a given distance from the determined ablation location;
        for each of the identified voxels that are within the given distance from the determined ablation location, increment the tissue necrosis values as a function of both i) distance from the determined ablation location and ii) at least one parameter to generate a total tissue necrosis value for each voxel, wherein the at least one parameter includes at least one of an ablation power level, an ablation delivery duration, a tissue contact force, a lesion-size index, and a force-time integral associated with an ablation procedure, a tissue type, and a total amount of energy delivered;
        render at least one lesion on the geometric surface model based on the total tissue necrosis values such that a center of the at least one lesion is rendered differently than portions of the lesion further away from the center of the lesion; and
        display the geometric surface model and the at least one rendered lesion.

2. The system of claim 1, wherein to render at least one lesion on the geometric surface model, the system is configured to render the at least one lesion directly on the geometric surface model.

3. The system of claim 1, wherein to render at least one lesion on the geometric surface model, the system is configured to render the at least one lesion on an overlay layer that is displaced relative to the geometric surface model.

4. The system of claim 1, wherein to create a 3D texture map, the system is configured to create a 3D texture map including voxels each having a tissue necrosis value and a tissue temperature value.

5. The system of claim 4, wherein the system is further configured to:
    increment the tissue temperature values as a function of temperature measured during an ablation procedure to generate a total tissue temperature value for each voxel; and
    render the at least one lesion based on the total tissue temperature values.

6. The system of claim 1, wherein to render at least one lesion on the geometric surface model, the system is configured to render the at least one lesion such that a border zone of the at least one lesion is transparent further from the center of the at least one lesion and opaque closer to the center of the at least one lesion.

7. The system of claim 1, wherein to render at least one lesion on the geometric surface model, the system is configured to render the at least one lesion such that the center of the at least one lesion is rendered in a first color and a border zone of the at least one region is rendered in a second, different color.

8. A computer-implemented method of rendering lesions on a geometric surface model of a geometric structure, the method comprising:
    creating a three-dimensional (3D) texture map including a plurality of voxels each having a tissue necrosis value;
    determining an ablation location;
    identifying, from the plurality of voxels, all voxels that are within a given distance from the determined ablation location;
    for each of the identified voxels that are within the given distance from the determined ablation location, incrementing the tissue necrosis values as a function of both i) distance from the determined ablation location and ii) at least one parameter to generate a total tissue necrosis value for each voxel, wherein the at least one parameter includes at least one of an ablation power level, an ablation delivery duration, a tissue contact force, a lesion-size index, and a force-time integral associated with an ablation procedure, a tissue type, and a total amount of energy delivered;

rendering at least one lesion on the geometric surface model based on the total tissue necrosis values such that a center of the at least one lesion is rendered differently than portions of the lesion further away from the center of the lesion; and displaying the geometric surface model and the at least one rendered lesion.

9. The method of claim 8, wherein rendering at least one lesion on the geometric surface model comprises rendering at least one lesion directly on the geometric surface model.

10. The method of claim 8, wherein rendering at least one lesion on the geometric surface model comprises rendering at least one lesion on an overlay layer that is displaced relative to the geometric surface model.

11. The method of claim 8, wherein creating a 3D texture map comprises creating a 3D texture map including voxels each having a tissue necrosis value and a tissue temperature value.

12. The method of claim 11, further comprising:

incrementing the tissue temperature values as a function of temperature measured during an ablation procedure to generate a total tissue temperature value for each voxel; and rendering the at least one lesion based on the total tissue temperature values.

13. A processing apparatus for rendering lesions on a geometric surface model of a geometric structure, the processing apparatus configured to:

create a three-dimensional (3D) texture map including a plurality of voxels each having a tissue necrosis value;

determine an ablation location;

identify, from the plurality of voxels, all voxels that are within a given distance from the determined ablation location;

for each of the identified voxels that are within the given distance from the determined ablation location, increment the tissue necrosis values as a function of both i) distance from the determined ablation location and ii) at least one parameter to generate a total tissue necrosis value for each voxel, wherein the at least one parameter includes at least one of an ablation power level, an ablation delivery duration, a tissue contact force, a lesion-size index, and a force-time integral associated with an ablation procedure, a tissue type, and a total amount of energy delivered;

render at least one lesion on the geometric surface model based on the total tissue necrosis values such that a center of the at least one lesion is rendered differently than portions of the lesion further away from the center of the lesion; and display the geometric surface model and the at least one rendered lesion.

14. The processing apparatus of claim 13, wherein to render at least one lesion on the geometric surface model, the processing apparatus is configured to render the at least one lesion directly on the geometric surface model.

15. The processing apparatus of claim 13, wherein to render at least one lesion on the geometric surface model, the processing apparatus is configured to render the at least one lesion on an overlay layer that is displaced relative to the geometric surface model.

16. The processing apparatus of claim 13, wherein to create a 3D texture map, the processing apparatus is configured to create a 3D texture map including voxels each having a tissue necrosis value and a tissue temperature value.

* * * * *